US006990455B2

(12) United States Patent
Vozick et al.

(10) Patent No.: US 6,990,455 B2
(45) Date of Patent: Jan. 24, 2006

(54) COMMAND AND CONTROL USING SPEECH RECOGNITION FOR DENTAL COMPUTER CONNECTED DEVICES

(75) Inventors: David Vozick, Mt. Kisco, NY (US); James Johnson, Ringwood, NJ (US)

(73) Assignee: AFP Imaging Corporation, Elmsford, NY (US)

( * ) Notice: Subject to any disclaimer, the term of this patent is extended or adjusted under 35 U.S.C. 154(b) by 573 days.

(21) Appl. No.: 09/924,831

(22) Filed: Aug. 8, 2001

(65) Prior Publication Data

US 2003/0033151 A1 Feb. 13, 2003

(51) Int. Cl.
*G10L 21/00* (2006.01)

(52) U.S. Cl. ............. 704/275; 704/276; 704/270; 704/270.1; 704/251

(58) Field of Classification Search .......... 704/270, 704/275, 276, 251, 231, 252–254, 270.1; 379/88.01, 88.04; 348/734; 381/110; 382/229
See application file for complete search history.

(56) References Cited

U.S. PATENT DOCUMENTS

| | | | |
|---|---|---|---|
| 5,440,606 A | | 8/1995 | Faul et al. |
| 5,924,069 A | * | 7/1999 | Kowalkowski et al. ..... 704/270 |
| 6,032,120 A | | 2/2000 | Rock et al. |
| 6,047,257 A | * | 4/2000 | Dewaele ............... 250/581 |
| 6,101,338 A | * | 8/2000 | Bernardi et al. ........... 396/287 |
| 6,133,904 A | * | 10/2000 | Tzirkel-Hancock ........ 345/156 |
| 6,157,705 A | * | 12/2000 | Perrone ............... 379/88.01 |
| 6,766,297 B1 | | 7/2004 | Lamer |
| 6,785,358 B2 | | 8/2004 | Johnson |

OTHER PUBLICATIONS

Lai et al., ("Medspeak : report creation with continuous speech recognition", Conference proceedings on Human factors in computing systems, 1997, ACM Press, pp. 431-438).*

Krapichler et al., ("Virtual reality and multimedia human-computer interaction in Medicine", 1998 IEEE Workshop on Multimedia Signal processing, pp. 193-202).*

Guerrouad ("Voice control in the surgery room", Images of the Twenty-first century, Proceedings of the Annual International Conference of the IEEE Engineering in Medicine and Biology, vol. 3, pp. 904-905).*

Teel et al., ("Voice-enabled structured medical reporting", Conference on Human factors and computing systems, 1998, ACM Press, pp. 595-602).*

* cited by examiner

*Primary Examiner*—Vijay Chawan
(74) *Attorney, Agent, or Firm*—Cooper & Dunham LLP

(57) ABSTRACT

Tools (in the form of apparatus, systems and methods) for hands-free command and control of a dental computer imaging system are provided. A speech recognition unit converts to electronic speech data a voice command received through a microphone to select for viewing, for a selected dental patient, one of a plurality of dental images stored in a computer storage device. A command and control processor causes the selected dental image to be retrieved from the storage device and then displayed on a display monitor.

18 Claims, 3 Drawing Sheets

COMMAND AND CONTROL USING SPEECH RECOGNITION FOR DENTAL COMPUTER CONNECTED DEVICES

BACKGROUND

The present disclosure relates to dental computer connected devices. In particular, the disclosure relates to using speech recognition in command and control for dental computer connected devices.

Computers are used increasingly in dental clinics, offices, teaching and training institutions to operate an expanding variety of devices and applications (hereinafter "dental computer connected devices"), such as, but not limited to, digital intra-oral radiography, panoramic radiography, cephalometric radiography, intra-oral video, cosmetic imaging manipulation, digital FOTI (fiber-optic trans-illumination) imaging, intra-oral spectrometry and color matching, digital periodontic probes, scanned input images, computerized intercom and telephone, intra-office cameras, and practice management.

The conventional methods of inputting data to and controlling the dental computer connected devices through the computer by operating a keyboard, mouse, touch screen monitor and/or other manually operated input-output (I/O) devices have some significant drawbacks when used in a dental environment. For example, manual manipulation of an I/O device by a dentist or dental technician while the dentist/technician is attending to a patient may be impractical since the computer must be conveniently positioned near the patient while not interfering with the dentist/technician's movement in attending to the patient.

It has been proposed to control mechanical components of an X-ray system according to voice commands detected through speech recognition. A user of the proposed system can control, for example, positioning of a dental chair/light and/or mechanical movement of X-ray system components by issuing a spoke command.

Others have proposed attaching to a computerized medical image dictated comments detected using speech recognition. In the proposed system, a physician, for example, provides her/his comments by speaking into a microphone while reviewing a medical image. The oral comments are converted to text through speech recognition, and the text is thereafter associated and stored with the image.

There are, however, many other aspects of dental office practice that may be made more efficient through computer speech recognition. For example, there are circumstances in which a dentist needs to refer to one or more of a patient's dental images, while attending to the patient. Conventional dental computer systems generally require manual operation of computer I/O devices, such as a mouse and/or keyboard, to specify a computer stored dental image to be retrieved. Since both hands of the dentist/technician often are needed for attending to a patient, the dentist typically would need to switch back and forth between attending to the patient and operating the computer, which may be time consuming. Further, switching back and forth between patient and hand operated I/O devices results in complications regarding infection control.

SUMMARY OF THE DISCLOSURE

The present disclosure provides an apparatus for hands-free command and control of a dental imaging system having a display monitor, a microphone and a storage device storing dental images for a selected dental patient. The apparatus comprises, according to one embodiment, a speech recognition unit and a command and control processor. The speech recognition unit converts to electronic speech data a voice command received through the microphone to select one of the dental images for viewing. The command and control processor causes the selected dental image to be retrieved from the storage device and then displayed on the display monitor.

The present disclosure also provides a dental imaging system comprising, according to one embodiment, a microphone, a display monitor, a storage device, and a speech recognition command unit. The storage device stores dental images for a selected dental patient. The speech recognition command unit converts to electronic speech data a voice command received through the microphone to select one of the dental images for viewing, and processes the electronic speech data to cause the selected dental image to be retrieved from the storage device and then displayed on the display monitor. The microphone may be wireless.

The present disclosure also provides a method of hands-free command and control of a dental imaging system. The method, according to one embodiment, comprises converting to electronic speech data a voice command from a user through a microphone to select for viewing one of a plurality of dental images stored in a computer storage device, and processing the electronic speech data to cause the selected dental image to be retrieved from the computer storage device and then displayed on a display monitor.

The dental images may include intra-oral images, panoramic dental images, FOTI images and periodontic images. Thumbnail representations of the dental images may be displayed for selection by the user for the selected dental patient. The dental images may be acquired from one of a dental computer connected device, video camera, digital scanner or X-ray storage device and stored in the storage device.

The storage device, in one embodiment, is connected to a computer network. In another embodiment, the storage device is remotely located and connected through a network. In any event, text, audio and video data also may be stored in the storage device and available for selection to be displayed.

In one embodiment, the command and control processor, after the selected dental image is retrieved from the storage device and displayed on the display monitor, and in response to a second voice command received through the microphone and converted by the speech recognition unit, causes the selected dental image to be further processed according to the second voice command. In another embodiment, the command and control processor, after the selected dental image is retrieved from the storage device and displayed on the display monitor, causes a voice interface through a speaker to provide a set of options, for selection by a user, for further processing the selected dental image. Also, the command and control processor may cause a voice interface through a speaker to provide a voice prompt to guide a user through selection of an appropriate dental image. The command and control processor may be remotely located and connected through a network.

The speech recognition unit, in one embodiment, includes a hardware module electronically coupled to the command and control processor. In another embodiment, the speech recognition unit comprises a client-server speech recognition system.

BRIEF DESCRIPTION OF THE DRAWINGS

The above and numerous other features of the present disclosure would be more readily understood from the following detailed description by referring to the accompanying drawings wherein.

DETAILED DESCRIPTION OF THE DISCLOSURE

The present disclosure provides tools (in the form of apparatus, systems and methods) which use computerized voice recognition to enable a dentist or dental technician to specify, through spoken commands, dental images to be retrieved from storage in a computer system and displayed and/or otherwise processed, without requiring the dentist/technician to manually operate computer I/O devices. Thus, the dentist/technician can continue to use her/his hands for attending to the patient, without risking contamination by operating the I/O devices. The tools may include hardware, software and combinations of hardware and software.

Figure 1:
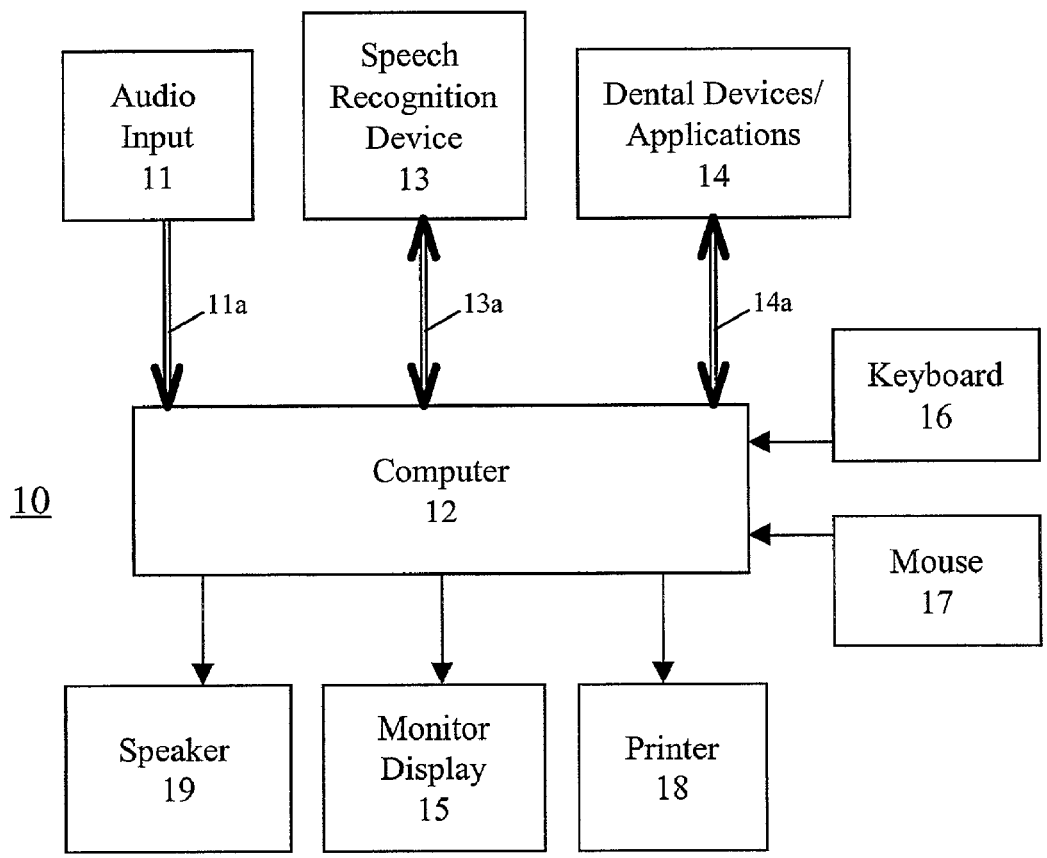
FIG. 1 shows a block diagram of a dental computer imaging system according to an embodiment of the present disclosure; A

A dental computer imaging system 10, according to an embodiment of the present disclosure, will be described with reference to FIG. 1. System 10 includes audio input device 11, computer 12, speech recognition unit 13, dental devices and applications 14, and conventional computer I/O devices, such as display monitor 15, keyboard 16, mouse 17, printer 18 and speaker 19.

An apparatus for hands-free command and control of a dental computer imaging system, according to an embodiment of the present disclosure, includes speech recognition unit 13 and command and control processor 12. The speech recognition unit 13 converts to electronic speech data a voice command received through microphone 11 to select one of the dental images for viewing. The command and control processor 12 causes the selected dental image to be retrieved from a computer storage device (described below) and then displayed on display monitor 15. The command and control processor 12 coupled to the speech recognition unit 13 may provide interface control and data input for computer connected dental devices and applications 14 (hardware and software) used in dental clinics for diagnosis and/or treatment of patients. Thus, for a patient being attended, a dentist/technician can, by using spoken commands, specify selected computer dental records (including images, text, audio and video) to be retrieved from computer storage, without manual operation of the computer and associated I/O devices. The retrieved records can then be displayed, manipulated, enhanced, restored, printed, transmitted, duplicated, etc.

Figure 2:
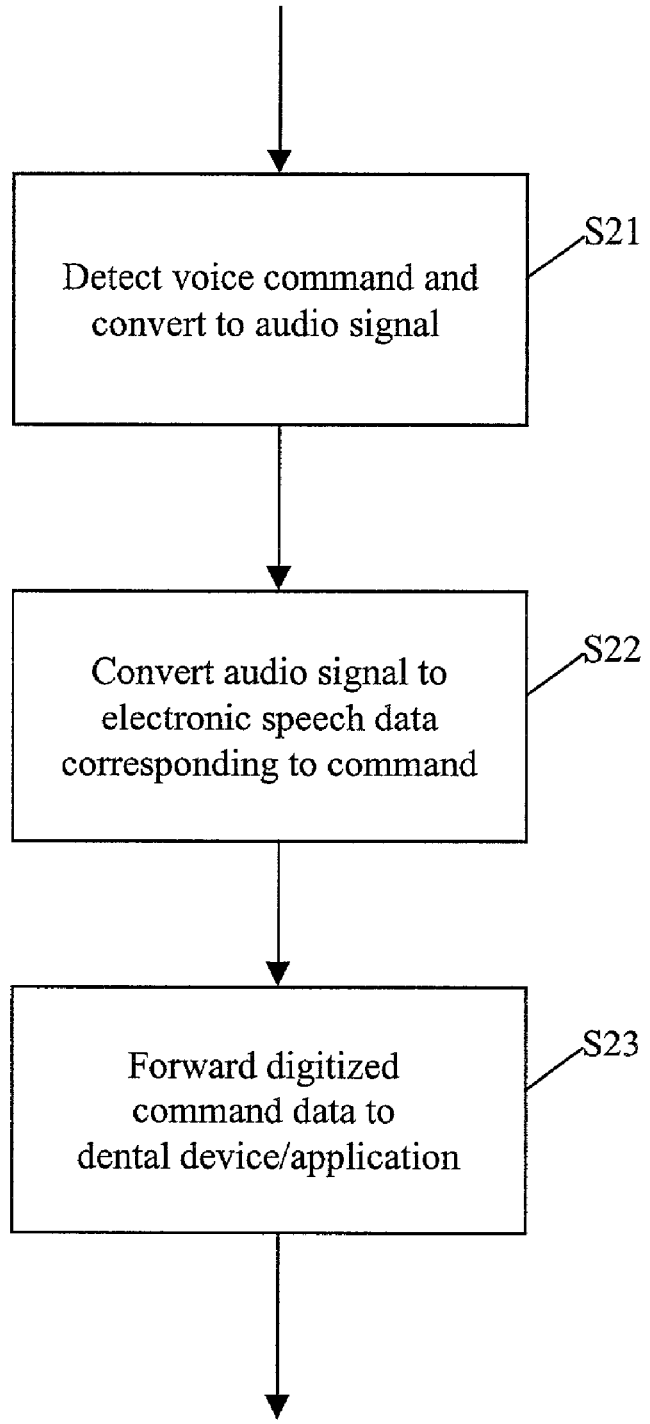
FIG. 2 shows a flow chart corresponding to a method for hands-free command and control of the dental computer imaging system shown in FIG. 1.

A method for hands-free command and control of the dental computer imaging system will be discussed with reference to FIGS. 1 and 2. When a user (for example, a dentist, dental technician, etc.) speaks into audio input device 11 (for example, a wired or wireless microphone) to direct the computer to retrieve a patient's records, the audio input device 11 detects the voice commands (step S21), converts it to a corresponding audio signal, and transmits the audio signal through a wired or wireless transmission medium 11a to computer 12. Computer 12 forwards the received audio signal to speech recognition system 13. The audio signal may be digitized along this process by microphone 11, computer 12, or speech recognition system 13. In any event, speech recognition unit 13 translates the audio signal to electronic speech data (step S22), such as text or other forms of useful computer data, corresponding to the spoken commands.

Computer 12 receives the digital data corresponding to the spoken commands from speech recognition system 13. As a command and control processor for dental devices/applications 14, computer 12 communicates the digitized commands to the appropriate dental devices/applications (step S23), and receives acknowledgments, responses and data from the dental devices/applications, through, in accordance with one embodiment, transmission medium 14a. Transmission medium 14a may be wired or wireless, and may use any of many appropriate communication protocols known in the art. In another embodiment, selected dental applications 14 are resident in/on computer 12.

The response from the dental devices/applications may include a set of options for selection by the user. The set of options are converted by the user interface into an appropriate form for presentation to the user through, for example, a graphical interface and/or a voice interface.

Computer 12 typically is a personal computer, but alternatively may be, for example, a workstation computer, a notebook computer, or a handheld computing device, such as a personal digital assistant (PDA). Computer 12 comprises a processor, memory, one or more storage drives, and one or more interfaces such as a network interface and interfaces with the I/O devices. The computer storage may include local storage such as, for example, a floppy disk drive, compact disc (CD) or digital versatile disc (DVD) drive, a hard disk, etc., or remote storage such as on a storage area network (SAN). The network interface includes the appropriate devices (for example, Ethernet card, modem, wireless modem, etc.) for interfacing with one or more wired or wireless networks, such as a LAN (local area network), a wireless LAN, a WAN (wide area network), an intranet, an extranet, the Internet, and/or any combinations of such networks.

In an embodiment in which computer 12 communicates with the dental devices/applications through a wireless communication link, computer 12 is provided with a wireless interface for communicating through the wireless communication link. One of a number of wireless interfaces (e.g., Bluetooth), such as for an infrared optical link or radio frequency (e.g., spread spectrum RF) link, known in the art may be used.

Computer 12 also typically includes, in addition to an operating system, software components such as a user interface (graphical, voice, etc.) and interfaces for controlling the hardware components, image management functions and other dental software packages, such as within dental devices and applications 14. The software components generally also include assorted device drivers, including a wireless communication driver if a wireless interface is provided.

The user interface may include a graphic interface and a voice interface. The graphic interface, coupled to the voice interface and input devices, such as keyboard 16, mouse 17 and/or other pointing devices, that may be used by the operator as an alternative means for input of commands and data, outputs visual information, such as text, images, etc., to display monitor 15 and/or printer/plotter 18 (through respective drivers). The voice interface is coupled to microphone 11 and speech recognition system 13 to facilitate the conversion of voice commands, detected by microphone 11, to digitized commands to dental devices and application 14. The voice interface may also be coupled to speaker 19 to provide a voice prompt to guide the user through, for example, the record selection process.

The software components may be stored on a floppy disk, CD or another storage medium, and installed on the computer. The software components alternatively (or also) may be communicated through the network interface via a network, such as the Internet, and/or a wireless transmission medium. Further, each software component may comprise one or more segments, subsets of which are retrieved, from the computer hard disk or via the network or transmission medium, as need arises.

Dental devices and applications 14 may comprise hardware, software or a combination of hardware and software. Dental devices and applications 14 may include, but are not limited to, digital intra-oral radiography, panoramic radiography, cephalometric radiography, intra-oral video, cosmetic imaging manipulation, digital FOTI imaging, intra-oral spectrometry and color matching, digital periodontic probes, scanned input images, computerized intercom and telephone, intra-office cameras, and practice management tools.

The dental devices and applications, in accordance with one embodiment, may share a common computer database for storing patient records. In another embodiment, each device and application may have its own database, with the computer storing a computerized patient record having pointers/links to corresponding entries in the respective databases.

Speech recognition system 13 may comprise hardware, software or a combination of hardware and software. In accordance with one embodiment, the speech recognition unit is software executed on computer 12. In another embodiment, the speech recognition system includes special purpose hardware adapted for use on or with computer 12. For example, the special purpose hardware may be a circuit board (or cartridge, module, etc.) that is plugged into computer 12. In another embodiment, computer 12 with appropriately loaded software is a client coupled to voice recognition server 13. Speech recognition methodologies are known in the art and embodied, in, for example, several commercially products (hardware and/or software). Accordingly, in order to preserve clarity, a discussion of voice recognition theory is not included herein.

Figure 3:
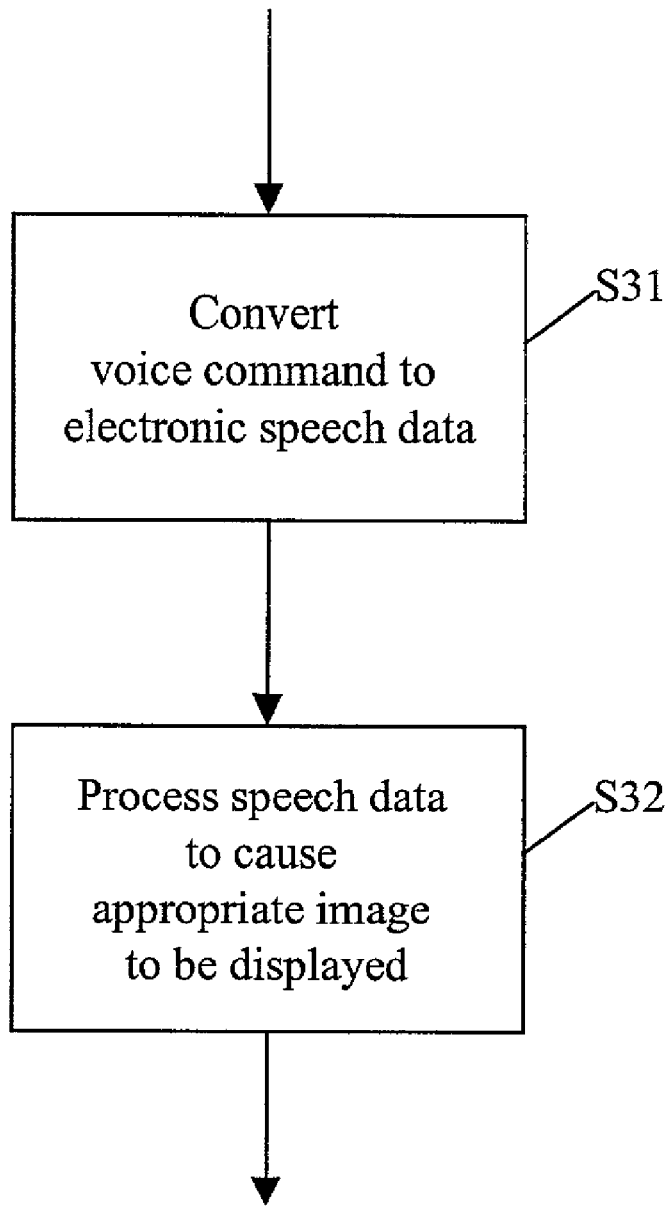
FIG. 3 shows a flow chart corresponding to a method for hands-free command and control of a dental computer imaging system, according to an embodiment of the present disclosure.

A methodology for hands-free command and control of a dental imaging system, according to an embodiment of the present disclosure (shown in FIG. 3), regardless whether implemented in software, hardware, or a combination, comprises converting to electronic speech data a voice command from a user through the microphone to select one of the dental images for viewing (step S31), and processing the electronic speech data to cause the selected dental image to be retrieved from the storage device and then displayed on the display monitor (step S32).

While embodiments of the present disclosure have been described in detail above, it should be understood that the disclosure is not limited to the precise embodiments described.

For example, computer 12 may be remotely located relative to the dental devices/applications. Thus, computer 12 may communicate the digitized command to, and receive responses from, dental devices/applications 14 through a network via the network interface (describe above).

Other improvements and modifications which become apparent to persons of ordinary skill in the art after reading this disclosure, the drawings and the appended claims are deemed within the spirit and scope of the present disclosure.

What is claimed is:

1. An apparatus for hands-free command and control of a dental imaging system having a display monitor, a microphone and a storage device storing a plurality of dental images corresponding to a selected dental patient, comprising:
    a speech recognition unit which converts to electronic speech data a voice command received through the microphone to select one of the plurality of dental images for viewing; and
    a command and control processor for the electronic speech data received from said speech recognition unit, wherein said command and control processor causes the selected dental image to be retrieved from the storage device and then displayed on the display monitor.

2. The apparatus of claim 1, wherein thumbnail representations of the plurality of dental images corresponding to the selected dental patient are displayed for selection by the user.

3. The apparatus of claim 1, wherein the plurality of dental images include intra-oral images, panoramic dental images, FOTI images and periodontic images.

4. The apparatus of claim 1, wherein text, audio and video data are also stored in the storage device and available for selection to be displayed.

5. The apparatus of claim 1, wherein the dental images are acquired from one of a dental computer connected device, video camera, digital scanner or X-ray storage device and stored in the storage device.

6. The apparatus of claim 1, wherein the storage device is connected to a computer network.

7. The apparatus of claim 1, wherein the storage device is remotely located and connected through a network.

8. The apparatus of claim 1, wherein the command and control processor is remotely located and connected through a network.

9. The apparatus of claim 1, wherein the microphone is wireless.

10. The apparatus of claim 1, wherein after the selected dental image is retrieved from the storage device and displayed on the display monitor, the command and control processor, in response to a second voice command received through the microphone and converted by said speech recognition unit, causes the selected dental image to be further processed according to the second voice command.

11. The apparatus of claim 1, wherein after the selected dental image is retrieved from the storage device and displayed on the display monitor, the command and control processor causes a voice interface through a speaker to provide a set of options, for selection by a user, for further processing the selected dental image.

12. The apparatus of claim 1, wherein the command and control processor causes a voice interface through a speaker to provide a voice prompt to guide a user through selection of an appropriate dental image.

13. The apparatus of claim 1, wherein the speech recognition unit includes a hardware module electronically coupled to the command and control processor.

14. The apparatus of claim 1, wherein the speech recognition unit comprises a client-server speech recognition system.

15. A dental imaging system, comprising:

a microphone;

a display monitor;

a storage device, wherein the storage device stores a plurality of dental images corresponding to a selected dental patient; and a speech recognition command unit which converts to electronic speech data a voice command received through said microphone to select one of the plurality of dental images for viewing, and processes the electronic speech data to cause the selected dental image to be retrieved from said storage device and then displayed on said display monitor.

16. The system of claim 15, wherein the microphone is wireless.

17. A method of hands-free command and control of a dental imaging system, comprising the steps of:

converting to electronic speech data a voice command from a user through a microphone to select for viewing one of a plurality of dental images stored in a storage device for a selected dental patient; and processing the electronic speech data to cause the selected dental image to be retrieved from the storage device and then displayed on a display monitor.

18. The method of claim 17, wherein the microphone is wireless.

* * * * *